United States Patent [19]

Hurt

[11] 4,287,189
[45] Sep. 1, 1981

[54] O,S-DIALKYL O-OXYSULFONYLPHENYL PHOSPHOROTHIOLATES AND PHOSPHORODITHIOATES

[75] Inventor: William S. Hurt, Collegeville, Pa.

[73] Assignee: Rohm and Haas Company, Philadelphia, Pa.

[21] Appl. No.: 133,219

[22] Filed: Mar. 24, 1980

Related U.S. Application Data

[63] Continuation-in-part of Ser. No. 680,330, Apr. 26, 1976, abandoned, which is a continuation-in-part of Ser. No. 587,510, Jun. 16, 1975, abandoned.

[51] Int. Cl.$^3$ .................... C07D 143/68; A61K 31/66
[52] U.S. Cl. ................................. 424/210; 424/215; 424/216; 424/225; 260/456 P
[58] Field of Search .................... 260/456 P; 424/210, 424/215, 216, 225

[56] References Cited

U.S. PATENT DOCUMENTS

| | | | |
|---|---|---|---|
| 3,374,293 | 3/1968 | Heiss et al. | 424/216 |
| 3,419,620 | 12/1968 | Becher et al. | 424/215 |
| 3,825,636 | 7/1974 | Kishino et al. | 424/210 |
| 3,839,511 | 10/1974 | Kishino et al. | 424/210 |
| 3,898,334 | 8/1975 | Kishino et al. | 424/210 |
| 3,966,920 | 6/1976 | Riebel et al. | 424/210 |
| 3,969,444 | 7/1976 | Oswald et al. | 424/210 |

FOREIGN PATENT DOCUMENTS

| | | | |
|---|---|---|---|
| 43-14933 | 6/1968 | Japan | 260/456 P |
| 1165846 | 10/1969 | United Kingdom | 260/456 P |

*Primary Examiner*—Nicky Chan
*Attorney, Agent, or Firm*—Terence P. Strobaugh; Bernard J. Burns

[57] ABSTRACT

This invention relates to novel organophosphorothiolates and phosphorodithioates of the formula:

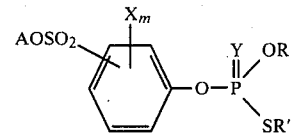

wherein
R is a $(C_1-C_4)$ alkyl group;
R' is a $(C_3-C_6)$ alkyl group;
Y is an oxygen atom or sulfur atom;
X is a halogen atom, a $(C_1-C_5)$ alkyl group, or a $(C_1-C_5)$ alkoxy group;
m is an integer from 0 to 3; and
A is
  (a) a $(C_1-C_5)$ alkyl group;
  (b) a $(C_1-C_5)$ alkyl group substituted with up to three halogen atoms;
  (c) a $(C_5-C_6)$ cycloalkyl group;
  (d) a $(C_7-C_{10})$ aralkyl group, the aryl portion of which is optionally substituted with up to three halogen atoms, cyano groups, nitro groups, $(C_1-C_5)$ alkyl groups, $(C_1-C_5)$ alkoxy groups, or $(C_1-C_5)$ alkylthio groups; or
  (e) an aryl group of the formula:

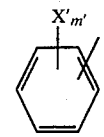

wherein
X' is a halogen atom, a nitro group, a cyano group, a $(C_1-C_5)$ alkyl group, a $(C_1-C_5)$ alkoxy group or a $(C_1-C_5)$ alkylthio group; and
m' is an integer from 0 to 3;

to compositions containing them and to methods of using them to control pests.

17 Claims, No Drawings

O,S-DIALKYL O-OXYSULFONYLPHENYL PHOSPHOROTHIOLATES AND PHOSPHORODITHIOATES

This application is a continuation-in-part application of U.S. Ser. No. 680,330 filed Apr. 26, 1976 now abandoned, which was a continuation-in-part of U.S. Pat. No. 587,510, filed June 16, 1975, now abandoned.

The present invention relates to novel organophosphorothiolates and phosphorodithioates having pesticidal activity, especially acaricidal and insecticidal activity, to compositions containing them, and to methods of using them to control various harmful pests. In addition to possessing outstanding pesticidal activity, compounds of the present invention possess a combination of desirable characteristics not possessed by known organophosphorus pesticides. These characteristics include activity against organophosphorus resistant species, residual activity, low toxicity to warm-blooded animals and low phytotoxicity for economically important plant species. These novel compounds can be represented by the formula:

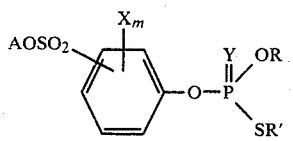

wherein
R is a ($C_1$-$C_4$) alkyl group, preferably methyl or ethyl;
R' is a ($C_3$-$C_6$) alkyl group, preferably a ($C_3$-$C_5$) alkyl group of the formula:

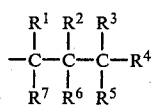

wherein
$R^1$-$R^7$ are individually hydrogen, methyl or ethyl, preferably hydrogen or methyl;
Y is an oxygen or sulfur atom;
X is a halogen atom, preferably chlorine; a ($C_1$-$C_5$) alkyl group, preferably methyl; or a ($C_1$-$C_5$) alkoxy group, preferably methoxy;
m is an integer from 0 to 3; and
A is a ($C_1$-$C_5$) alkyl group; a ($C_1$-$C_5$) alkyl group substituted with up to three halogen atoms, preferably chlorine; a ($C_5$-$C_6$) cycloalkyl group; a ($C_7$-$C_{10}$) aralkyl, preferably benzyl, group, the aryl portion of which is optionally substituted with up to three halogen atoms, preferably chlorine, nitro groups, cyano groups, ($C_1$-$C_5$) alkyl groups, preferably methyl, ($C_1$-$C_5$) alkoxy groups, preferably methoxy, or ($C_1$-$C_5$) alkylthio groups, preferably methylthio; or an aryl group of the formula:

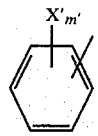

wherein
X' is a halogen atom, preferably chlorine; a nitro group; a cyano group; a ($C_1$-$C_5$) alkyl group, preferably methyl; a ($C_1$-$C_5$) alkoxy group, preferably methoxy; or a ($C_1$-$C_5$) alkylthio group, preferably methylthio; and
m' is an integer from 0 to 3.

As used in the specification and claims, the terms "alkyl", "alkoxy", "alkylthio", and "aralkyl" are intended to include branched chain as well as straight chain groups. Representative alkyl, alkoxy, alkythio and aralkyl groups include, for example, methyl, ethyl, n-propyl, sec-butyl, isobutyl, pentyl, neopentyl, 2-methylpentyl, n-hexyl, methoxy, ethoxy, propoxy, sec-butoxy, pentoxy, methylthio, ethylthio, isopropylthio, n-propylthio, isobutylthio, tert-butylthio, pentylthio, benzyl, phenethyl, α-methylphenethyl, and the like.

The organophosphorothiolates and phosphorodithioates described above can exist in their isomeric forms, wherein the $AOSO_2$ group of Formula I is attached to the benzene ring in a position which is ortho, meta or para, preferably para, to the phosphorothiolate or phosphorodithioate group.

The preferred compounds of this invention, i.e. those having especially enhanced acaricidal and insecticidal activity can be represented by the following formula:

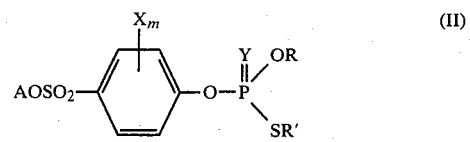

wherein
R is a methyl or ethyl group;
R' is a n-propyl, n-butyl, isobutyl, or sec-butyl group;
Y is an oxygen or sulfur atom;
X is a halogen atom, preferably chlorine, or a ($C_1$-$C_5$) alkyl group, preferably methyl;
m is zero or 1, preferably zero;
A is a ($C_1$-$C_5$) alkyl group, preferably methyl, or an aryl group of the formula:

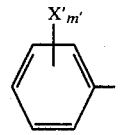

wherein
X' is a halogen atom, preferably chlorine, a nitro group, a cyano group, a ($C_1$-$C_5$) alkyl group, preferably methyl, a ($C_1$-$C_5$) alkoxy group, preferably methoxy, or a ($C_1$-$C_5$) alkylthio group, preferably methylthio, and
m' is zero, 1 or 2, preferably zero or 1.

Typical compounds within the scope of this invention include the following:
O-[4-(methoxysulfonyl)phenyl]O-methyl S-n-propyl phosphorothiolate
O-[3-(n-butoxysulfonyl)phenyl]O-ethyl S-n-propyl phosphorothiolate
O-[4-(2'-chloroethoxysulfonyl)phenyl]O-ethyl S-n-propyl phosphorothiolate
O-[3-(cyclohexyloxysulfonyl)phenyl]O-ethyl S-n-propyl phosphorothiolate O-[4-(benzyloxysulfonyl)phenyl]O-ethyl S-n-propyl phosphorothiolate O-[4-(4'-chlorobenzyloxysulfonyl)phenyl]O,S-di-n-propyl phosphorothiolate O-[4-(2',4'-dimethylbenzyloxysulfonyl)phenyl]O-ethyl S-n-propyl phosphorothiolate O-Ethyl S-isobutyl O-[3-(phenethoxysulfonyl)-phenyl]phosphorothiolate O-Methyl O-[4-(phenoxysulfonyl)phenyl]S-n-propyl phosphorothiolate O-Ethyl O-[3-(phenoxysulfonyl)phenyl]S-n-propyl phosphorothiolate O-Ethyl O-[2-(phenoxysulfonyl)phenyl]S-n-propyl phosphorothiolate O-n-Butyl S-sec-butyl O-[3-(phenoxysulfonyl)-phenyl]phosphorothiolate O-Ethyl S-isobutyl O-[4-(phenoxysulfonyl)phenyl]-phosphorothiolate O-Ethyl S-n-pentyl O-[2-(phenoxysulfonyl)phenyl]-phospborothiolate S-n-Butyl O-[4-(4'-chlorophenoxysulfonyl)phenyl]O-ethyl phosphorothiolate O-Ethyl S-isobutyl O-[4-(4'-nitrophenoxysulfonyl)-phenyl]phosphorothiolate S-sec-Butyl O-Ethyl O-[4-(4'-nitrophenoxysulfonyl)-phenyl]phosphorothiolate O-Ethyl O-[4-(4'-methoxyphenoxysulfonyl)phenyl]S-n-propyl phosphorothiolate O-[4-(4'-cyanophenoxysulfonyl)phenyl]O-ethyl S-n-propyl phosphorothiolate O-[2,4-dichloro-6-(2',4'-dichlorophenoxysulfonyl)-phenyl]O-ethyl S-n-propyl phosphorothiolate O-[2-chloro-4-(4'-nitrophenoxy)phenyl]O-ethyl S-n-propyl phosphorothiolate O-Ethyl O-[4-(3'-fluorophenoxysulfonyl)-3-methyl phenyl]S-isobutyl phosphorothiolate O-[3-n-butyl-4-(phenoxysulfonyl)phenyl]O-ethyl S-n-propyl phosphorothiolate O-[4-(2'-bromophenoxysulfonyl)-3-methoxyphenyl-]O-ethyl S-n-pentyl phosphorothiolate O-[4-(4'-chloro-2'-methyl phenoxysulfonyl)phenyl-]O-ethyl S-n-propyl phosphorothiolate O-[4-(4'-bromo-2'-chlorophenoxysulfonyl)phenyl]O-ethyl S-sec-butyl phosphorothiolate O-Ethyl O-[4-(2'-methylphenoxysulfonyl)phenyl]S-n-propyl phosphorothiolate O-Ethyl S-n-propyl O-[4-(2',4',5'-trichlorophenoxysulfonyl)-phenyl]phosphorothiolate O-Ethyl-S-isobutyl O-[4-(4'-methylphenoxysulfonyl)-2,5-dichlorophenyl]phosphorothiolate O-isopropyl O-[4-(4'-methoxyphenoxysulfonyl)-phenyl]S-n-propyl phosphorothiolate O-Ethyl S-n-hexyl O-[3-(phenoxysulfonyl)-2,5-dimethylphenyl]phosphorothiolate O-Methyl O-[4-methoxy-2-(phenoxysulfonyl)-phenyl]S-n-propyl phosphorothiolate O-Ethyl O-[4-(phenoxysulfonyl)phenyl]S-n-propyl phosphorodithiolate O-Ethyl S-isobutyl O-[2-(phenoxysulfonyl)phenyl]-phosphorodithiolate O-Ethyl O-[4(4'-methylthiophenoxysulfonyl)-phenyl]S-n-propyl phosphorodithioate and the like.

The compounds of this invention can be prepared by reacting a phenol with an O,S-dialkylphosphorochloridothiolate or phosphorochloridodithioate. The general reaction can be represented by the following equation:

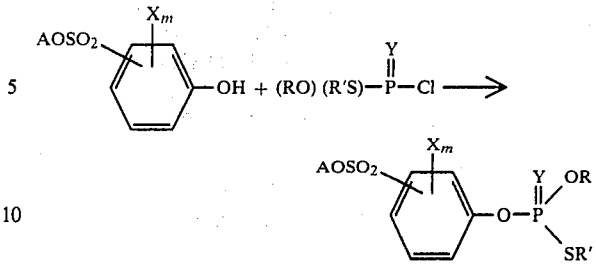

wherein A,Y,R,R',X and m are as defined for Formula I.

An acid acceptor such as tertiary amine or an alkali carbonate or hydroxide can be employed as a scavenger in this preparation. Representative acid acceptors include pyridine, trimethylamine, triethylamine, dimethylaniline, lithium carbonate, sodium hydroxide, potassium hydroxide and the like. Generally, a substantially equimolar ratio of reactants is preferred but an excess of any of the reactants can be employed. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile and the like.

Suitable solvents include benzene, toluene, heptane, methylethyl ketone, acetone, ethyl ether, acetonitrile and dioxane. The reaction is generally conducted in a temperature range of about $-10°$ to about $100°$ C. or more, and preferably in the range of about $0°$ to about $60°$ C.

In addition to the above procedure, the compounds of this invention can be prepared by reacting an alkali phenoxide with an O,S-dialkylphosphorochloridothiolate or phosphorochloridodithioate. This reaction can be represented by the following equation:

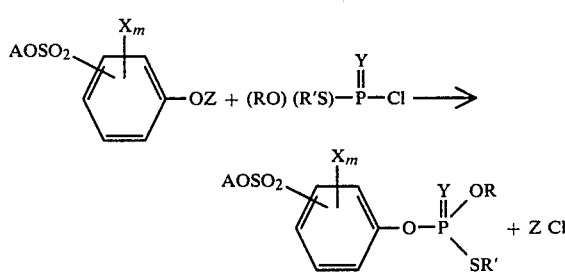

wherein A,R,R',X,Y, and m are as defined for Formula I and Z is an alkali metal, such as sodium, potassium or lithium.

Reaction conditions, including choice of solvents, temperature, and molar ratios correspond to the conditions described above for the reaction of an O,S-dialkylphosphorochloridothiolate or phosphorochloridodithiolate with a phenol, except that there is no need to employ an acid acceptor in this reaction.

All of the starting materials used in the preparation of the compounds of this invention are known compounds or are readily prepared by adaptations of known routes. For example, 4-phenoxysulfonyl phenols are prepared by reacting a p-carbethoxyoxybenzenesulfonyl chloride[described by M. Hulguist et al., J. Am. Chem. Soc., 73, 2556 (1951)], or a similarly protected phenol, with an alkali phenoxide, to give the O-ethyl O-phenoxysulfonyl phenyl carbonate from which the carbethoxy protecting group is removed by treatment with mild base.

Alternately, 4-phenoxysulfonyl phenols are available by reactng methoxybenzene sulfonyl chloride with a phenol in the presence of an acid scavenger such as pyridine to give phenyl 4-methoxybenzenesulfonate from which the methyl group is removed by the method of Burton [J. Chem. Soc., 16 (1945)].

The O,S-dialkylphosphorochloridothiolates are prepared by reacting an alkylsulfenyl chloride with a dialkychlorophosphite [A. F. Lippman, J. Org. Chem., 30, 3217 (1965)]. The phosphorodithioates are prepared by the method described in Japanese Patent No. 72/05536.

The following examples are given by way of illustration and are not to be considered as limitations of the present invention.

EXAMPLE I

Preparation of 4-phenoxysulfonylphenol

Sodium phenoxide, 9.0 g. (0.078 mole) is added in portions to a solution of 20 g. (0.076 mole) of 4-ethoxycarbonyloxybenzenesulfonyl chloride in 250 ml. of dry benzene. The slurry is brought to reflux (80° C.) for 1.5 hours and then allowed to stir at room temperature overnight. The reaction is followed by thin layer chromatography, additional sodium phenoxide is added as needed, and the reaction is refluxed until complete. The slurry is then cooled to room temperature and filtered to remove sodium chloride. The filtrate is concentrated to give 22.3 g. (88%) of the desired benzene sulfonate as an oil of suitable purity for the next reaction. The 4-ethoxycarbonyloxybenzene sulfonate (22.3 g., 0.069 mole) is taken up in 120 ml. of ethanol and stirred at 20° C. while a solution of 5.3 g. (0.08 mole) of potassium hydroxide in 50 ml. of ethanol is added dropwise. After two hours at room temperature, the solution is brought to 40° C. for 30 minutes and then concentrated in vacuo. The residue is taken up in 250 ml. of water (pH=10), extracted once with ether, acidified to pH 1 with 10 ml. of concentrated hydrochloric acid and then extracted three times with 200 ml. portions of chloroform. The chloroform extracts are combined, dried over sodium sulfate and concentrated in vacuo to give 15.9 g. (91%) of the phenol as an oil which crystallizes on standing; m.p.=114°–116.5° after recrystallization from xylene.

EXAMPLE II

Preparation of O-Ethyl O-[4-(phenoxysulfonyl)phenyl]S-n-propyl phosphorothiolate To a solution of 4.7 g. (0.019 mole) of 4-phenoxysulfonyl phenol in 40 ml. of acetonitrile is added a dispersion of 0.51 g. (0.021 mole) of sodium hydride in 10 ml. of acetonitrile at room temperature. The solution is stirred for 20 minutes at 25° C. Then, 4.9 g. (0.024 mole) of O-ethyl S-n-propyl phosphorochloridothiolate, is added dropwise over a period of 8 minutes at 25°–32° C. The solution is stirred overnight at 38°–45° C., and then filtered to remove sodium chloride and concentrated in vacuo to give 8.7 g. of yellow oil. Column chromatography of the oil on silica gel using butyl acetate/heptane as the eluant, gives 5.4 g. (68%) of the phosphorothiolate as a pale yellow oil, Analysis calculated (found) for $C_{17}H_{21}O_6PS_2$: C, 49.0 (48.9); H, 5.08 (5.44); P, 7.44 (7.08); S, 15.4 (15.5).

EXAMPLES III TO XIII

In a manner similar to that of Example II, the following compounds are likewise readily prepared:

O-Ethyl-O-[4-(4'-nitrophenoxysulfonyl)phenyl]S-n-propyl phosphorothiolate Analysis Calc. (found): C, 42.67 (42.67); H, 4.03 (4.04).

O-[4-(4'-chlorophenoxysulfonyl)phenyl]O-ethyl S-n-propyl phosphorothiolate Analysis Calc. (found): C, 45.29 (45.61); H, 4.47 (4.63).

O-Ethyl-O-[4-(methoxysulfonyl)phenyl]S-n-propyl phosphorothiolate Analysis Calc. (found): C, 40.67 (40.76); H, 5.40 (5.97).

O-[4-(4'-cyanophenoxysulfonyl)phenyl]O-ethyl S-n-propyl phoshorothiolate Analysis Calc. (found): C, 48.97 (48.98); H, 4.57 (4.90).

O-Ethyl-O-[4-(4'-methylthiophenoxysulfonyl)phenyl]S-n-propyl phosphorothiolate Analysis Calc. (found): C, 46.74 (47.62): H, 5.01 (5.35).

O-Ethyl-O-[4-(4'-methylphenoxysulfonyl)phenyl]S-n-propyl phosphorothiolate Analysis Calc. (found): C, 50.22 (49.69); H, 5.38 (5.61).

S-sec-Butyl O-ethyl O-[4-(phenoxysulfonyl)phenyl]-phosphorothiolate Analysis Calc. (found): C, 50.22 (50.77); H, 5.38 (5.42).

S-n-Butyl O-ethyl O-[4-phenoxysulfonyl)phenyl]-phosphorothiolate Analysis Calc. (found): C, 50.22 (50.38); H, 5.38 (5.42).

O-Ethyl S-isobutyl O-[4-(phenoxysulfonyl)phenyl]-phosphorothiolate Analysis Calc. (found): C, 50.22 (50.23); H, 5.38 (5.53).

O-Methyl O-[4-(4'-nitrophenoxysulfonyl)phenyl]S-n-propyl phosphorothiola Analysis Calc. (found): C, 42.67 (42.77) H, 4.03 (4.04).

O-Ethyl O-[4-(phenoxysulfonyl)phenyl]S-n-propyl phosphorodithiolate Analysis Calc. (found): C, 47.20 (47.70); H, 4.89 (5.33).

The novel organophosphorothiolates and phosphorodithioates of this invention are biocidally active. In particular, they are effective as acaricides and insecticides and as such exhibit a broad spectrum of activity. Certain compounds of this invention also possess activity as nematocides and fungicides, especially as phytopathogenic fungicides. Acaricidal, insecticidal and nematocidal evaluations are made on the following organisms:

| Common Name | Latin Name |
| --- | --- |
| Two-spotted spider mite (TSM) | Tetranychus urticae |
| Green peach aphid (GPA) | Myzus persicae |
| Mexican bean beetle (BB) | Epilachna varivestis |
| Southern armyworm (AW) | Spodoptera eridania |
| Southern corn rootworm (CRW) | Diabrotica undecimpunctata howardi |
| Boll weevil (BW) | Anthonomus grandis |
| House Fly | Musca domestica |
| Lone star tick | Amblyoma americanum |
| Southern root knot nematode | Meloidogyne incognita |

A test solution containing 600 ppm of test compound is made by dissolving the test compound in a solvent (acetone:methanol, 1:1), adding surfactant and then water to give an acetone:methanol:water system of 10:10:80. A 1:1 mixture of an alkylarylpolyether-alcohol (commercially available under the trademark Triton X-155) and a modified phthalic glycerol alkyd resin (commercially available under the trademark Triton B-1956) can be utilized at the equivalent of one ounce per gallon of test solution as a surfactant.

For the mite test, infested bean (*Phaseolus limeanus*) leaf discs (1.25 inches in diameter) containing about 50 mites and for green peach aphid tests, infested broccoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent killed is determined.

For the bean beetle and armyworm test, detached bean leaves on pieces of moistened filter paper are sprayed as above for the mite test in similar dishes and allowed to dry. One such dish is infested with 10 third instar Mexican bean beetle larvae, while another is infested with 10 third instar southern armyworm larvae. The dishes are covered. After holding for 48 hours, the percent killed is obtained.

For the boll weevil and house fly tests, half pint glass canning jars with a screened top are used. Food is supplied for the boll weevil (apple) and for the house fly (sugar water). The test insects consist of 10 adult boll weevils and 20 adult house flies. The jars containing the insects are sprayed using the turntable. The percent kill of boll weevil is determined 48 hours after the application. In the house fly test, a percent knockdown is determined one hour after application, the percent kill after 24 hours.

For the tick test, plastic Petri dish bottoms containing a piece of filter paper are sprayed with the test compounds. After the filter paper dries, a small quantity of water is pipetted into each dish to insure proper humidity. The dishes are then infested with about 50 lone star tick larvae and capped with tight-fitting plastic lids. After holding for 24 hours, the percent kill is obtained.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot in which three cucumber (*Cucumis sativus*) seeds are planted. About 23 days thereafter, the cucumber plants are removed from the soil and the root system examined for the presence of knots. A total of 25 knots or less is considered as a measure of control.

Ovicidal and larvicidal tests are conducted on representative compounds of this invention. These compounds demonstrate ovicidal and larvicidal activity.

For mite tests involving the two-spotted mite ova and larvae, bean leaf sections containing about 100 eggs are placed on moistened cotton in a Petri dish and sprayed on the turntable with a 150 ppm test solution. These are held for 6 days and examined under the microscope. Unhatched eggs and dead and live larvae are counted and the percent ovicidal and larvicidal activity are determined.

For tests involving the southern corn rootworm ova and larvae, two layers of 4.25 cm. filter papers are placed in small, Petri dishes, and sprayed on the turntable with a 600 ppm solution of the test compound and air dried. About 100 eggs in about one milliliter of water are pipetted onto the filter paper and the dishes covered. These are held for 6 days and examined under the microscope. The percent kill values for ova and larvae are determined.

Table I below shows the data obtained for representative compounds encompassed by the present invention utilizing test procedures disclosed above.

TABLE I

| Ex. No. | $LC_{50}{}^a$ (ppm) | | | | | | |
|---|---|---|---|---|---|---|---|
| | GPA | TSM | BB | AW | BW | CRW-O[b] | CRW-L[c] |
| II | 7.5 | 9.8 | 75 | 32 | 345 | >600 | 32 |
| III | 6.2 | 5 | 75 | 45 | >600 | >600 | 75 |
| IV | 2.5 | 2.9 | 75 | 75 | 138 | 142 | 4.1 |
| VI | 18 | 6.8 | 49 | 41 | >600 | >600 | 38 |
| VII | 6.4 | 2.4 | 162 | 27 | 550 | >600 | 130 |
| VIII | 7.5 | 20 | 150 | 75 | >600 | 550 | 33 |
| IX | 2.8 | 5.8 | 15 | 45 | 75 | 230 | 8.4 |
| X | 8.6 | 5 | 27 | 41 | >600 | >600 | 75 |
| XI | 1.3 | 6.6 | 26 | 49 | 75 | >600 | 142 |
| XII | 26 | 6.6 | 54 | 45 | 500 | >600 | 75 |
| XIII | 38 | 8 | 150 | 75 | 150 | >600 | 10 |

[a]Lethal concentration at which 50% of the pests are killed
[b]Corn rootworm ova
[c]Corn rootworm larva Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and to allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Some of the plant diseases controlled by compounds of this invention include, for example, wheat leaf rust (*Puccinia recondita*), bean powdery mildew (*Erysiphe polygoni*), grape downy milldew (*Plasmopora viticola*), and the like.

The compounds of the present invention are used for protection of plants and animals, including man, from the ravages of harmful and annoying pests or disease organisms which they may carry. The term "pest" as used herein is intended to include arthropods, such as insects and acarids in all stages of development, nematodes, fungi, such as phytopathogenic fungi, and the like. Generally, control of a living organism is achieved in accordance with this invention by application of the compounds in pesticidally effective amounts either directly to the pests to be controlled or to the loci to be freed of or protectedd from attack by such pests. For example, food, fiber, forage, forest, and ornamental crops and stored products thereof would represent plant protection loci. Treatment with compounds of this invention of domestic animals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

For use as pesticides the compounds of this invention can be used as solutions in organic solvents or formulations. For example, they can be formulated as wettable powders, emulsifiable concentrates, dusts, granular formulations or flowable emulsifiable concentrates. In such formulations, the organophosphorothiolates or phosphorodithioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The oranophosphorothiolate or phosphorodithioate can be taken up on or mixed with a finely particled solid carrier, as for example, clays, inorganic silicates, carbonates, and silicas. Organic carriers can also be employed. Dust concentrates are commonly made wherein organophosphorothiolates or phosphorodithioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The organophosphorothiolates or phosphorodithioates are usually present in the range of about 10 to about 80% by weight and surfactants from about 0.5 to about 10% by weight.

One convenient method of preparing a solid formulation is to impregnate the organophosphorothiolate or phosphorodithioate onto the solid carrier by means of a volatile solvent such as acetone. In this manner, adjuvants, such as activators, adhesives, plant nutrients, synergists and various surfactants also can be incorporated.

Emulsifiable concentrate formulations can be prepared by dissolving organophosphorothiolates or phosphorodithioates of this invention in an agronomically acceptable organic solvent and adding a solvent-soluble emulsifying agent. Suitable solvents are usually waterimmiscible and can be found in the hydrocarbon, ketone, ester, alcohol and amide groups of organic solvents. Mixtures of solvents are commonly employed. The surfactants useful as emulsifying aents can constitute 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the organophosphorothiolate or phosphorodithioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purposes for such application, the organophosphorothiolates or phosphorodithioates being utilized, the frequency of dissemination and the like.

By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

Many of the above formulations can be utilized on animals for control of parasites.

For use as insecticides and acaricides, dilute sprays can be applied at concentrations of about 0.001 to about 20 pounds of the active organophosphorothiolate or phosphorodithioate ingredient per 100 gallons of spray. They are usually applied at about 0.01 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a nematocide or as a soil insecticide, the organophosphorothiolates or phosphorodithiolates can be applied as a solid formulation, by broadcasting, sidedressing, soil incorporation or seed treatment. The application rate can be from about 1 to about 50 pounds per acre. For soil incorporation, the compounds of this invention can be mixed with the soil at a rate of about 2 to about 100 ppm.

For use as a fungicide, the organophosphorothiolates or phosphorodithioates can be applied as fungicidal sprays by methods commonly employed, such as conventional high-gallonage hydraulic sprays, low-gallonage sprays, air-blast sprays, serial sprays and dusts. The dilution and rate of application will depend upon the type of equipment employed, the method of application and diseases to be controlled, but the preferred effective amount is usually about 0.1 lb. to 50 lbs. per acre of the active ingredient. As a fungicidal seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula:

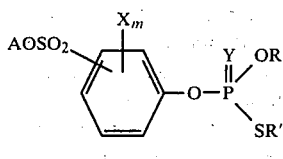

wherein
R is a (C$_1$-C$_4$) alkyl group;
R' is a (C$_3$-C$_6$) alkyl group;
Y is an oxygen atom or a sulfur atom;
X is a halogen atom, a (C$_1$-C$_5$) alkyl group, or a (C$_1$-C$_5$) alkoxy group;
m is an integer from 0 to 3; and
A is
  (a) a (C$_1$-C$_5$) alkyl group substituted with up to three halogen atoms;
  (b) a (C$_5$-C$_6$) cycloalkyl group;
  (c) a (C$_7$-C$_{10}$) aralkyl group, the aryl portion of which is optionally substituted with up to three halogen atoms, nitro groups, cyano groups, (C$_1$-C$_5$) alkyl groups, (C$_1$-C$_5$) alkoxy groups or (C$_1$-C$_5$) alkylthio groups; or
  (d) an aryl group of the formula:

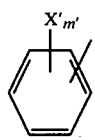

wherein
X' is a halogen atom, a nitro group, a cyano group, a (C$_1$-C$_5$) alkyl group, a (C$_1$-C$_5$) alkoxy group or a (C$_1$-C$_5$) alkylthio group, and
m' is an integer from 0 to 3.

2. A compound according to claim 1 wherein R' is a (C$_3$-C$_5$) alkyl group of the formula:

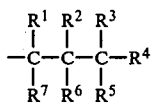

wherein R$^1$-R$^7$ are individually hydrogen, methyl, or ethyl.

3. A compound according to claim 2 wherein the AOSO$_2$ group is attached to the benzene ring in a position which is para to the point of attachment of the phosphorothiolate or phosphorodithioate group.

4. A compound according to claim 3 having the formula:

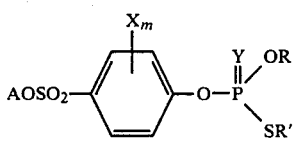

wherein
R is a methyl or ethyl group;
R' is a n-propyl, n-butyl, isobutyl, or sec-butyl group;
Y is an oxygen or sulfur atom;
Y is a halogen atom or a (C$_1$-C$_5$) alkyl group;
m is zero or 1;
A is an aryl group of the formula

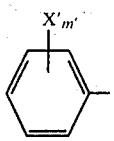

wherein
X' is a halogen atom, a nitro group, a cyano group, a (C$_1$-C$_5$) alkyl group, a (C$_1$-C$_5$) alkoxy group, or a (C$_1$-C$_5$) alkylthio group; and
m' is zero, 1 or 2.

5. A compound according to claim 4 wherein m is zero.

6. A compound according to claim 5 having the formula:

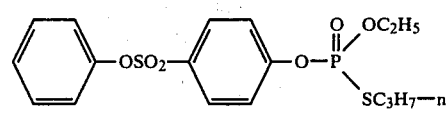

7. A compound according to claim 5 having the formula:

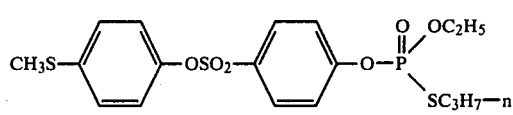

8. A compound according to claim 5 having the formula:

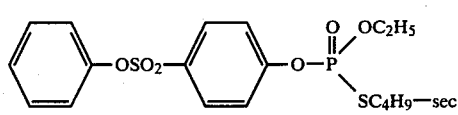

9. A compound according to claim 5 having the formula:

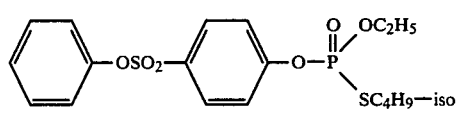

10. A compound according to claim 5 having the formula:

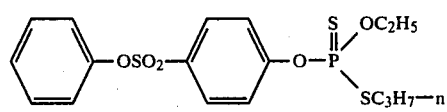

11. A pesticidal composition comprising a pesticidally effective amount of a compound according to claim 1 and an agronomically acceptable carrier.

12. A pesticidal composition comprising a pesticidally effective amount of a compound according to claim 5 and an agronomically acceptable carrier.

13. A method of controlling pests which comprises applying directly to the pests or to the loci to be freed of or protected from attack by such pests, a pesticidally effective amount of the composition of claim 11.

14. A method of controlling pests which comprises applying directly to the pests or to the loci to be freed of or protected from attack by such pests, a pesticidally effective amount of the compound of claim 1.

15. A method according to claim 13 wherein the pests are acarids, insects, nematodes, or phytopathogenic fungi.

16. A method according to claim 15 wherein the pests are acarids.

17. A method according to claim 15 wherein the pests are insects.

* * * * *